(12) United States Patent
Salisbury et al.

(10) Patent No.: US 8,082,775 B2
(45) Date of Patent: Dec. 27, 2011

(54) SYSTEMS AND METHODS FOR SIMULATING AN ENGINE ENVIRONMENT

(75) Inventors: Cliff James Salisbury, Peoria, IL (US); Jade Marie Katinas, Chillicothe, IL (US); Leonard George Wheat, Manito, IL (US); Jennifer Joan Leustek, Metamora, IL (US); Jason Adam Smid, Melbourne, FL (US); Philip Carl Spengler, Washington, IL (US); Mark Andrew McElroy, Peoria, IL (US); Beth Ann Sebright, Chillicothe, IL (US)

(73) Assignee: Caterpillar Inc., Peoria, IL (US)

( * ) Notice: Subject to any disclaimer, the term of this patent is extended or adjusted under 35 U.S.C. 154(b) by 397 days.

(21) Appl. No.: 12/155,062

(22) Filed: May 29, 2008

(65) Prior Publication Data

US 2009/0299712 A1 Dec. 3, 2009

(51) Int. Cl.
*G01M 15/02* (2006.01)
(52) U.S. Cl. ................................. 73/114.55; 73/118.02
(58) Field of Classification Search ............... 73/114.55, 73/114.56, 116.01, 116.02, 118.01, 118.02
See application file for complete search history.

(56) References Cited

U.S. PATENT DOCUMENTS

| | | | |
|---|---|---|---|
| 2,829,826 A | 4/1958 | Wolin et al. | |
| 3,670,561 A | 6/1972 | Hundere | |
| 3,886,791 A * | 6/1975 | Grossman | 73/150 R |
| 4,335,072 A | 6/1982 | Barnett et al. | |
| 4,599,217 A | 7/1986 | Winston et al. | |
| 4,605,923 A | 8/1986 | Marshall | |
| 5,287,731 A | 2/1994 | Florkowski et al. | |
| 5,302,300 A * | 4/1994 | Porri | 210/774 |
| 5,370,799 A | 12/1994 | Oddo et al. | |
| 5,401,661 A | 3/1995 | Florkowski et al. | |
| 5,584,360 A | 12/1996 | Wedeven | |
| 5,636,708 A | 6/1997 | Wedeven et al. | |
| 6,004,910 A * | 12/1999 | Bloch et al. | 508/294 |
| 6,007,826 A | 12/1999 | Benita et al. | |
| 6,862,562 B1 | 3/2005 | Trieber et al. | |
| 7,127,959 B2 | 10/2006 | Blum et al. | |
| 2005/0021218 A1 * | 1/2005 | Bhargava et al. | 701/108 |
| 2007/0137292 A1 | 6/2007 | Xian et al. | |
| 2007/0186889 A1 | 8/2007 | Schweiger | |
| 2009/0145211 A1 * | 6/2009 | Schneider | 73/114.55 |
| 2010/0146943 A1 * | 6/2010 | Muramatsu et al. | 60/286 |
| 2010/0147056 A1 * | 6/2010 | Stolle et al. | 73/86 |

OTHER PUBLICATIONS

ESPEC North America, Inc., "Platinous Temperature and Humidity Chambers," brochure, ES-7577, Dec. 2006 (8 pages).

* cited by examiner

*Primary Examiner* — Eric S McCall
(74) *Attorney, Agent, or Firm* — Finnegan, Henderson, Farabow, Garrett & Dunner LLP

(57) ABSTRACT

A system for simulating an engine environment during engine operation is disclosed. The system includes a surface. The system also includes a liquid delivery device configured to deliver a liquid to the surface. The system further includes a temperature controller operably coupled to the surface, and the system is configured to cause condensation of a fluid on the surface.

18 Claims, 2 Drawing Sheets

SYSTEMS AND METHODS FOR SIMULATING AN ENGINE ENVIRONMENT

TECHNICAL FIELD

This disclosure is directed to systems and methods for simulating an engine environment and, more particularly, to systems and methods for simulating an engine environment during engine operation to facilitate the analysis of lubricant in an internal combustion engine environment.

BACKGROUND

An internal combustion engine, such as, for example, a compression ignition engine, spark-ignition engine, or natural gas engine, may include a cylinder block defining at least one cylinder and a head including one or more intake and exhaust valves. The one or more intake and exhaust valves may be housed within a valve cover. The valve cover may serve to ensure that a cavity that is defined by the head and a body of the valve cover is adequately sealed from the surrounding atmosphere to prevent vapors from the engine from being expelled directly into the environment.

During operation of the engine, energy input such as, for example, heat and/or vibration, may cause an emulsion formed by moisture (e.g., from water), engine lubricant, and/or fuel to form under the valve cover. Such emulsion formation is undesirable and may cause, for example, metal component corrosion and/or other engine damage. As a result, it may be desirable to determine parameters under which emulsion may form in an engine environment, for example, under a valve cover, during engine operation. Thus, it may be desirable to simulate an engine environment for the purpose of, for example, determining conditions that may lead to the formation of emulsion under an engine valve cover during operation, and/or to analyze engine lubricant compositions that reduce and/or eliminate emulsion formation.

Past efforts have been made to simulate an engine environment for testing of oxidation resistance of engine lubricant. For example, U.S. Pat. No. 5,287,731 issued to Florkowski et al. on Feb. 22, 1994 ("the '731 patent"), discloses an apparatus for testing engine lubricating oil under simulated engine operating conditions including a tank with an interior space containing a quantity of engine lubricating oil. The tank includes devices to introduce oil oxidizing agents to the oil. The apparatus includes a metal rod extending centrally through the enclosure so that oil passes along its outer surface, and the rod is selectively heated so that oxidation deposits form along the rod. Examination and analysis of the rod and its deposits permit rating of a particular lubricant for its oxidation resistant properties.

Although the apparatus disclosed in the '731 patent purportedly provides simulated engine operating conditions, it fails to provide a simulated engine environment for analyzing emulsion formation that may occur during engine operation.

The devices and methods of the present disclosure are directed towards improvements in the existing technology.

SUMMARY

In one aspect, the present disclosure is directed to a system for simulating an engine environment during engine operation. The system may include a surface. The system may also include a liquid delivery device configured to deliver a liquid to the surface. The system may further include a temperature controller operably coupled to the surface, and the system may be configured to cause condensation of a fluid on the surface.

In another aspect, the present disclosure is directed to a method of simulating an engine environment during engine operation. The method may include providing a surface. The method may also include delivering a lubricant to the surface. The method may further include condensing a fluid on the surface.

In yet another aspect, the present disclosure is directed to a method for improving an engine lubricant using a simulated engine environment. The method may include providing a surface, providing a chamber enclosing the surface, and delivering an engine lubricant to the surface. The method may also include condensing a fluid on the surface, and recording at least one of a plurality of parameters associated with the chamber. The method may further include analyzing the engine lubricant, and determining changes to a composition of the engine lubricant based on the analysis.

DETAILED DESCRIPTION

Figure 1:
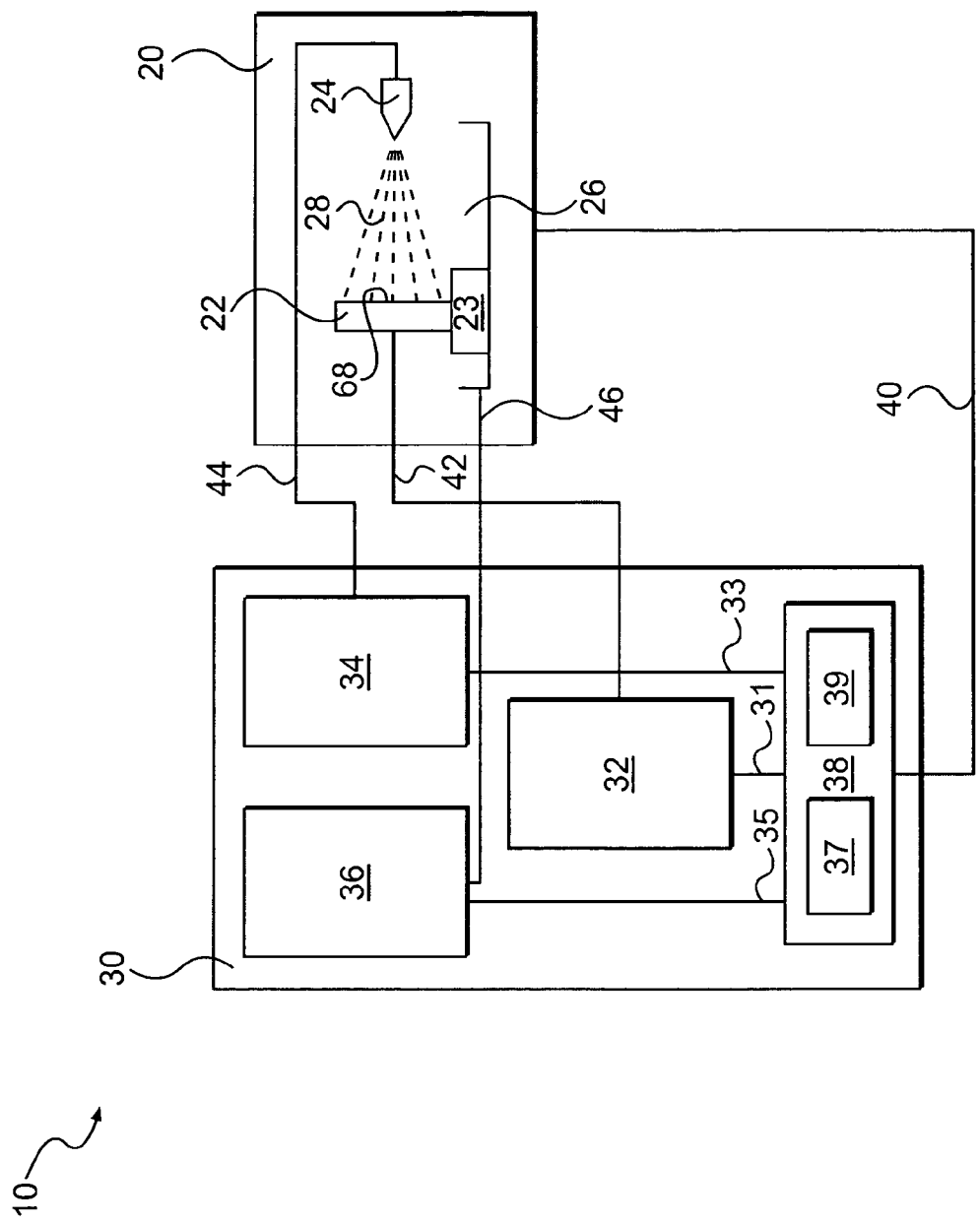
FIG. 1 is a schematic diagram of an exemplary embodiment of an engine environment simulator.

An exemplary embodiment of an engine environment simulator 10 is schematically illustrated in FIG. 1. Engine environment simulator 10 may be used to simulate the environment inside an internal combustion engine during operation, for example, the conditions (e.g., the temperature, humidity, and/or compositions of fluids and/or gases present) inside a valve cover during operation of an internal combustion engine. Engine environment simulator 10 may include a chamber 20 and a control station 30. For example, chamber 20 may provide an enclosure for simulating an engine environment during engine operation, and control station 30 may facilitate control of various parameters for affecting the simulated engine environment in chamber 20.

As shown in FIG. 1, exemplary chamber 20 may include a test panel 22, a liquid delivery device 24, and a collector 26. For example, test panel 22 may be generally rectangular and planar in shape. Alternatively, test panel 22 may assume other shapes, such as, for example, generally circular or polygonal. According to some embodiments, test panel 22 may be in the form of, for example, a cold plate. It is contemplated that test panel 22 may be any appropriate panel where condensation of a fluid (e.g., water) may occur on the surface of the panel. Likewise, it is contemplated that test panel 22 may represent any engine surfaces (i.e., internal engine surfaces) where emulsion might occur during engine operation. For example, test panel 22 may be configured to simulate an engine valve cover (e.g., an internal surface of an engine valve cover). Test panel 22 may be formed from, for example, aluminum, steel, iron, alloys, other suitable metals, and/or composite materials, etc.

Liquid delivery device 24 may be any suitable device configured to deliver a liquid 28 to a surface 68 of test panel 22. For example, liquid delivery device 24 may include one or more of a mister, a sprayer, a dispenser, etc. Liquid 28 may include, for example, one or more of fuel, engine lubricant, oil, or any liquid that may be present during the operation of an engine and may form emulsion with the condensed fluid. According to some embodiments, liquid delivery device 24 may be configured to provide control of the amount, temperature, and/or flow rate of liquid 28 being delivered to surface 68 of test panel 22 via, for example, control station 30. According to some embodiments, collector 26 may be disposed within chamber 20, so that collector 26 may collect any liquid, including but not limited to liquid mixture that may leave surface 68 of test panel 22 and/or liquid delivery device 24 during and/or following the operation of engine environment simulator 10. Collector 26 may be removable and the content of which may be discarded after collector 26 is removed from chamber 20. For example, collector 26 may include a drip pan, as shown in FIG. 1. Engine environment simulator 10 may also include a base member 23 that may be disposed between collector 26 and test panel 22. Base member 23 may serve to elevate test panel 22 to facilitate delivery of liquid 28 to surface 68 of test panel 22.

According to some embodiments, control station 30 may be configured to control a plurality of parameters that may affect formation of emulsion on test panel 22. The plurality of parameters may include conditions within chamber 20, such as, for example, humidity, air flow, and temperature, etc. The plurality of parameters may also include the temperature of test panel 22, the amount and/or rate of liquid 28 delivered via liquid delivery device 24, the composition of liquid 28, and/or the temperature of liquid 28, etc. Similarly, the plurality of parameters may also include the dew point for condensation to occur within chamber 20, for example, by controlling the humidity and temperature within chamber 20. It is contemplated that there may be other parameters that may affect the formation of emulsion on test panel 22, and the parameters listed above are not intended to be an exhaustive list. For example, different types of liquid 28 (e.g., different compositions of liquid 28) used during the operation of engine environment simulator 10 may affect the formation of emulsion in chamber 20. Thus, an operator of engine environment simulator 10 may operate engine environment simulator 10 with different types of liquid 28. According to some embodiments, engine environment simulator 10 may include one or more storage receptacles (not shown) for storing different types of liquid 28, and control station 30 may be configured to control the delivery of the different types of liquid 28. According to some embodiments, control station 30 may be configured to control one or more of the different parameters outlined above with the aid of, for example, an electronic control unit 38.

Control station 30 may be operably coupled to chamber 20 via various connectors. For example, as shown in FIG. 1, control station 30 may include a temperature controller 32, a liquid supply 34, and a separator 36. Temperature controller 32 may be operably coupled to test panel 22 via one or more connectors 42, and may be configured to control the temperature of test panel 22. For example, temperature controller 32 may include a reservoir (not shown), and connector(s) 42 may be configured to provide flow communication between the reservoir and test panel 22. For example, connector(s) 42 may include one or more (e.g., two as shown) liquid transfer tubes. According to some embodiments, test panel 22 may include one or more internal passages, for example, test panel 22 may be in the form of a hollow plate. Temperature controller 32 may be configured to control the temperature of test panel 22, for example, by circulating fluid (e.g., water and/or any appropriate liquid coolant) between the reservoir and test panel 22 via connector(s) 42. Alternatively, or in addition, temperature controller 32 may include an electric circuit, and connector(s) 42 may include a cable operably coupling the electric circuit to test panel 22. It is contemplated that temperature controller 32 and connector(s) 42 may be in any form configured to control the temperature of test panel 22.

According to some embodiments, liquid supply 34 may be operably coupled to liquid delivery device 24 via connector 44, as shown in FIG. 1. For example, connector 44 may include a liquid transfer tube, and control station 30 may be configured to control the amount and/or rate of liquid 28 supplied from liquid supply 34 to liquid delivery device 24. According to some embodiments, engine environment simulator 10 may include separator 36, which is operably coupled to chamber 20 via connector 46. Separator 36 may be configured to separate one or more constituent parts of a liquid mixture that may be present in chamber 20. Separator 36 may include a plurality of storage units (not shown), each unit configured to store each one of the constituent parts of the liquid mixture. The liquid mixture may include, for example, water, fuel, engine lubricant, mist of any of the aforementioned liquids, and/or other chemicals used to simulate an engine environment. Connector 46 may include one or more liquid and/or gas transfer tubes providing flow communication between chamber 20 and separator 36. The liquid mixture present in chamber 20 may be transferred to separator 36 via connector 46.

According to some embodiments, control station 30 may include electronic control unit 38. For example, electronic control unit 38 may include a controller 37 and a processor 39 (e.g., a microprocessor). Electronic control unit 38 may be operably coupled to temperature controller 32, liquid supply 34, and/or separator 36 via, for example, cables 31, 33, and 35, respectively. Electronic control unit 38 may be configured to control simulated engine environment conditions within chamber 20. For example, electronic control unit 38 may be operably coupled to chamber 20 via one or more connectors 40. According to some embodiments, controller 37 may be configured to control of a plurality of parameters that may affect the simulated engine environment, for example, that may relate to the formation of emulsion within chamber 20. In addition, processor 39 may be configured to facilitate the recording of data associated with one or more of the parameters that may affect formation of emulsion in chamber 20 during the operation of engine environment simulator 10.

According to some embodiments, data recorded by processor 39 may be used by electronic control unit 38 for controlling different parameters that may affect the formation of emulsion in engine environment simulator 10. For example, processor 39 may be configured to facilitate analysis of the recorded data, and processor 39 may send a signal representative of the analysis of the recorded data. The analysis may include an evaluation of the recorded data. For example, processor 39 may be configured to monitor the formation of emulsion on test panel 22. Processor 39 may also be configured to determine a time period during which emulsion may be formed on test panel 22. Electronic control unit 38 may be configured to control the different parameters that may affect the formation of emulsion in response to the signal sent by processor 39. According to some embodiments, an operator may analyze the recorded data. In some embodiments, an operator may control the different parameters that may affect the formation of emulsion with the aid of electronic control unit 38. It is contemplated that in response to the analysis of the recorded data, an additive (not shown) may be introduced to test panel 22. In some embodiments, the additive may eliminate the formation of emulsion on test panel 22. In some embodiments, the additive may separate the constituents of the emulsion formed on test panel 22 over a predetermined period of time.

Figure 2:
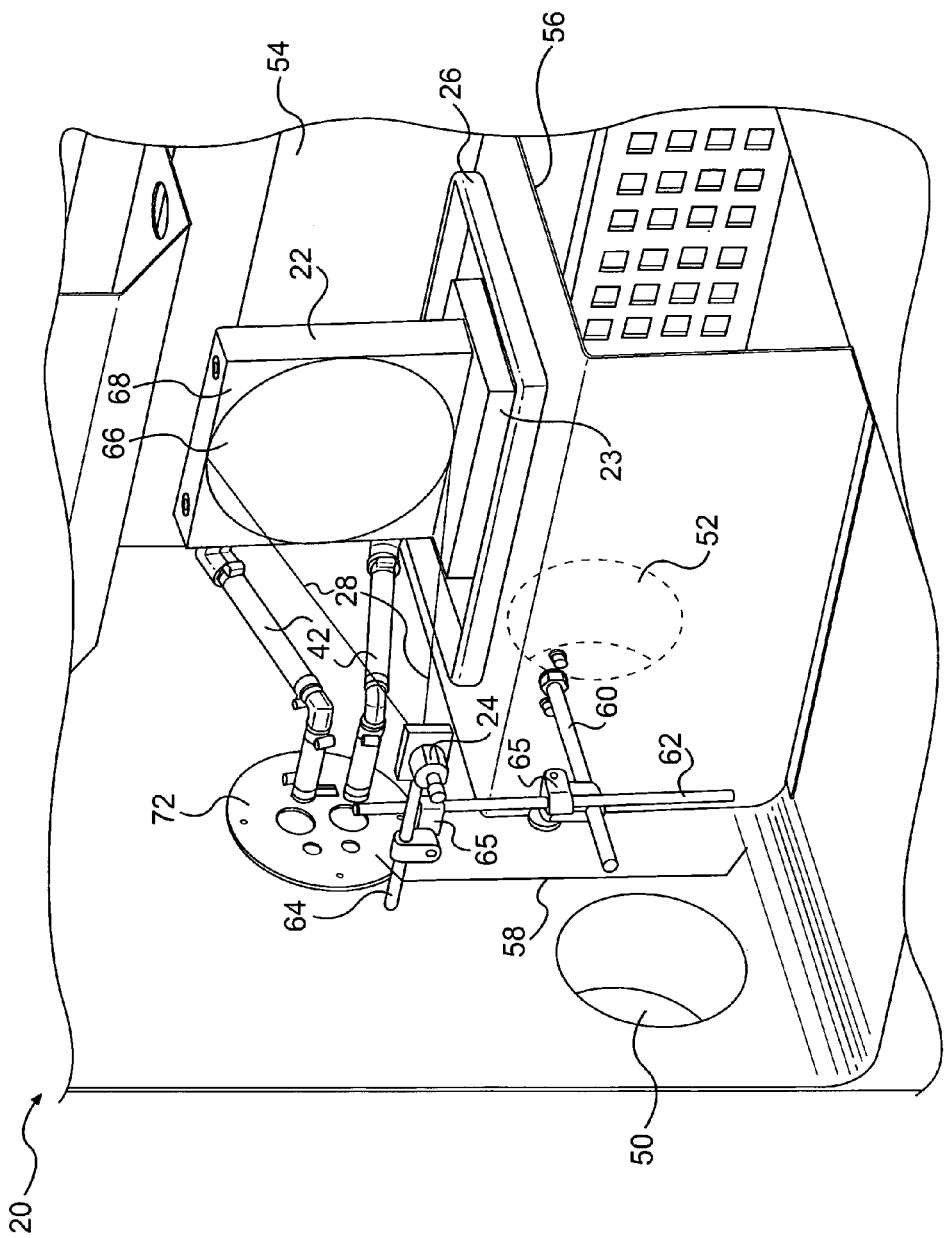
FIG. 2 is a schematic, perspective cutaway view of an exemplary embodiment of an engine environment simulator.

As shown in FIG. 2, exemplary chamber 20 may include an outlet 50, an air inlet 52, and an air diverter 54. Outlet 50 may be configured to remove the liquid mixture that may be present in chamber 20. Outlet 50 may include an opening configured to receive connector 46. Ambient air may enter chamber 20 via air inlet 52. Air diverter 54 may be configured to direct air flow within chamber 20. Other gases may be supplied to chamber 20 via one or more of air inlet 52 and other inlets in chamber 20 (not shown). For example, chamber 20 may include an exhaust inlet, where engine exhaust (or simulated engine exhaust) may enter chamber 20. In that case, the plurality of parameters that may affect formation of emulsion on test panel 22 may also include the engine exhaust flow within chamber 20.

According to the exemplary embodiment shown in FIG. 2, chamber 20 may include one or more support members configured to support different components that may be included in chamber 20. For example, chamber 20 may include a support member 56 that may provide structural support for collector 26. According to some embodiments, support member 56 may include a shelf. Chamber 20 may also include a support member 58 configured to provide structural support for liquid delivery device 24. For example, as illustrated in FIG. 2, support member 58 may include structural members 60, 62, and 64. Structural member 60 may extend substantially perpendicularly from support member 56 and structural member 62 may be generally perpendicular to structural member 60. Structural member 60 may be engaged with structural member 62, so that a portion of structural member 60 may overlap a portion of structural member 62. Similarly, structural member 64 may be generally perpendicular to structural member 62. Structural member 64 may be engaged with structural member 62, so that a portion of structural member 62 may overlap a portion of structural member 64. Support member 58 may also include fasteners 65 that may secure the engagements of structural members 60, 62, and 64. It is contemplated that support member 58 may be adjustable. For example, structural members 60, 62, 64, and fasteners 65 may be moved from a first position, where liquid delivery device 24 may be at a first distance and/or orientation relative to surface 68, to a second position, where liquid delivery device 24 may be at a second distance and/or orientation relative to surface 68. The first distance may be shorter (or less) than the second distance.

In the exemplary embodiment shown in FIG. 2, liquid delivery device 24 may be operably coupled to structural member 64 (e.g., to an end of structural member 64). Liquid delivery device 24 may be positioned within chamber 20, such that liquid 28 is delivered to an area 66 on surface 68 of test panel 22. According to some embodiments, area 66 may be generally circular in nature, although area 66 may have other shapes. The area of area 66 may be less than the area of surface 68. As illustrated in FIG. 2, base member 23 may be disposed between test panel 22 and collector 26, and base member 23 may serve to elevate the height of test panel 22, so that liquid 28 is delivered to area 66. According to some embodiments, chamber 20 may include a connecting plate 72 configured to receive connector(s) 42. For example, as shown in FIG. 2, connector(s) 42 may include two liquid transfer tubes, and connecting plate 72 may include two openings to receive connector(s) 42, for example, the two liquid transfer tubes.

INDUSTRIAL APPLICABILITY

The disclosed systems and methods for simulating an engine environment may be employed in various arrangements, for example, where observation of emulsion formation may be desirable. One skilled in the art will recognize that the disclosed simulation systems and methods may be used to simulate any enclosed engine environment, for example, to facilitate analysis of emulsion formation. For example, various exemplary embodiments disclosed herein may be used to simulate an engine environment for facilitating analysis of formation of emulsion under an engine valve cover.

In the exemplary embodiments of FIGS. 1 and 2, engine environment simulator 10 may simulate engine operation conditions that may result in the formation of emulsion under an engine valve cover. For example, test panel 22 may simulate an engine valve cover (e.g. an internal surface of an engine valve cover), and chamber 20 may represent the enclosed engine environment under the engine valve cover during operation of an internal combustion engine. Liquid 28 may include one or more of fuel, engine lubricant, oil, and/or any liquid that may be present during engine operation and may form emulsion with a condensed fluid (e.g., water). Chamber 20 may include liquid delivery device 24, which may be configured to deliver liquid 28 to surface 68 of test panel 22. The area of area 66 may be less than the area of surface 68. In addition, temperature controller 32 may be configured to control the temperature of test panel 22, and such temperature control may be used to cause, for example, condensation of fluid (e.g., of water) to be formed on surface 68. The condensation of fluid may further be controlled by controlling the humidity within chamber 20. An emulsion of the condensation and other fluids may be formed. For example, the emulsion may be formed with the condensation and liquid 28 on surface 68 of test panel 22.

Electronic control unit 38 may be configured to control a plurality of parameters that may affect the formation of emulsion, including but not limited to, humidity, air flow, exhaust flow, and temperature within chamber 20, temperature of test panel 22, amount and/or rate of liquid 28 delivered via liquid delivery device 24, and temperature of liquid 28, etc. By varying and/or controlling one or more of a plurality of such parameters, an operator of engine environment simulator 10 may be able to observe different conditions under which emulsion may be formed on test panel 22.

According to some embodiments, an operator may use engine environment simulator 10 to facilitate analysis of the status of an engine lubricant to vary the composition of an engine lubricant. For example, engine environment simulator 10 may be used to improve the performance of an engine lubricant by facilitating analysis of the effects of one or more such parameters on emulsion formation inside, for example, an engine valve cover. For example, the composition of engine lubricants and/or one or more of the parameters may be varied and the status of the engine lubricant and/or the formation of emulsion may be analyzed to identify engine lubricant compositions (e.g., the chemical structure and/or make-up of engine lubricants) that result in reduced emulsion formation inside an engine valve cover during engine operation.

According to some embodiments, electronic control unit 38 may include controller 37 and processor 39 that may be used to record data of the different parameters that may affect the formation of emulsion on test panel 22 during the operation of engine environment simulator 10. Data recorded by processor 39 may be analyzed to determine, for example, conditions that are more likely to lead to the formation of emulsion in an enclosed engine environment. According to some embodiments, controller 37 may control the different parameters based on the data recorded by processor 39, and controller 37 may be configured to control the different parameters to determine parameters that reduce or eliminate the formation of emulsion on test panel 22. According to some embodiments, controller 37 may be configured to introduce an additive (not shown) to test panel 22 based on the data recorded by processor 39. The additive may eliminate the formation of emulsion on test panel 22 and/or separate the constituents of the emulsion formed on test panel 22 over a predetermined period of time.

It will be apparent to those skilled in the art that various modifications and variations may be made to the exemplary engine environment simulator systems and methods of the present disclosure without departing from the scope of the disclosure. Other embodiments will be apparent to those skilled in the art from consideration of the specification and practice of the engine environment simulator systems and methods disclosed herein. It is intended that the specification and examples be considered as exemplary only, with a true scope of the disclosure being indicated by the following claims.

What is claimed is:

1. A system for analyzing formation of an emulsion, comprising:
   a test surface;
   a liquid delivery device configured to deliver a test liquid to the test surface;
   a temperature controller operably coupled to the test surface, wherein the temperature controller is configured to control a temperature of the test surface to cause condensation of a fluid on the test surface, the fluid and the test liquid being capable of forming the emulsion;
   a test chamber configured to enclose the test surface; and
   an electronic control unit operably coupled to the test chamber, wherein the electronic control unit is configured to control a plurality of parameters associated with the test chamber.

2. The system of claim 1, wherein the test liquid is selected from the group consisting of fuel, engine lubricant, oil, and combinations thereof.

3. The system of claim 1, wherein the plurality of parameters includes at least one of a humidity associated with the test chamber, a temperature associated with the test chamber, an air flow associated with the test chamber, an exhaust flow associated with the test chamber, a temperature of the test surface, an amount of the test liquid delivered onto the test surface, a delivery rate of the test liquid delivered to the test surface, and a composition of the test liquid delivered onto the test surface.

4. The system of claim 1, further including a processor configured to record data associated with at least one of the plurality of parameters associated with the test chamber.

5. The system of claim 4, wherein the electronic control unit is configured to control the plurality of parameters associated with the test chamber based on the data recorded by the processor.

6. A method for analyzing formation of an emulsion in a simulated engine environment, the method comprising:
   providing a test surface external to an internal combustion engine;
   delivering a test lubricant to the test surface; and
   condensing a fluid on the test surface by controlling a temperature of the test surface to cause condensation of the fluid on the test surface, the fluid and the test lubricant being capable of forming the emulsion.

7. The method of claim 6, wherein the test lubricant is selected from the group consisting of fuel, engine lubricant, oil and combinations thereof.

8. The method of claim 6, further including:
   providing a test chamber enclosing the test surface; and
   introducing air into the test chamber.

9. The method of claim 8, further including controlling a plurality of parameters associated with the test chamber.

10. The method of claim 9, wherein the plurality of parameters includes at least one of a humidity associated with the test chamber, a temperature associated with the test chamber, an air flow associated with the test chamber, a temperature of the test surface, an amount of the test lubricant delivered onto the test surface, a delivery rate of the test lubricant delivered to the test surface, and a composition of the test lubricant delivered onto the test surface.

11. The method of claim 9, further including recording data associated with at least one of the plurality of parameters.

12. The method of claim 11, further including controlling at least one of the plurality of parameters based on the recorded data.

13. A method for analyzing an engine lubricant using a simulated engine environment, the method comprising:
   providing a surface;
   providing a chamber enclosing the surface;
   delivering the engine lubricant to the surface;
   condensing a fluid on the surface;
   recording at least one of a plurality of parameters associated with the chamber; and
   analyzing at least one property associated with the engine lubricant, wherein analyzing the at least one property includes analyzing emulsion formation of the engine lubricant and the fluid on the surface.

14. The method of claim 13, wherein the engine lubricant is selected from the group consisting of fuel, oil, and combinations thereof.

15. The method of claim 13, wherein the plurality of parameters includes at least one of a humidity associated with the chamber, a temperature associated with the chamber, an air flow associated with the chamber, an exhaust flow associated with the chamber, a temperature of the surface, an amount of engine lubricant delivered to the surface, a rate of delivery of the engine lubricant to the surface, and the composition of the engine lubricant delivered to the surface.

16. The method of claim 13, further including generating at least one signal representative of an analysis of the plurality of parameters associated with the chamber, and controlling the plurality of parameters associated with the chamber in response to the at least one signal.

17. The method of claim 13, further including determining changes to a composition of the engine lubricant based on the analysis.

18. The method of claim 13, wherein providing a surface includes providing a surface that is not within an internal combustion engine.

* * * * *